United States Patent [19]

Duffett

[11] Patent Number: Plant 5,402

[45] Date of Patent: Feb. 5, 1985

[54] CHRYSANTHEMUM PLANT NAMED ECLIPSE

[75] Inventor: William E. Duffett, Salinas, Calif.

[73] Assignee: Yoder Brothers, Inc., Barberton, Ohio

[21] Appl. No.: 506,504

[22] Filed: Jun. 21, 1983

[51] Int. Cl.[3] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Eclipse having semi-incurved capitulum form; decorative capitulum type; deep lemon yellow ray floret color; diameter across face of capitulum ranging from 100 to 120 mm. at maturity; uniform nine week photoperiodic flowering response to short days; medium plant height when grown as a pinched, disbud pot mum; and a prolific, spreading branching pattern.

3 Drawing Figures

The present invention comprises a new and distinct cultivar of *Chrysanthemum morifolium,* Ramat., named Eclipse.

Eclipse is a product of a planned breeding program which had the objective of creating new chrysanthemum cultivars for pinched pot mum programs having decorative capitulum type, yellow floret color, nine week flowering response, and the ability to produce commercially acceptable quality in year round programs. Such traits in combination were not present or needed improvement in previously available commercial cultivars.

Eclipse was originated from a cross made in a controlled breeding program in Salinas, Calif. in 1979. The female parent was identified as 7520010, an unnamed yellow decorative seedling originated by the present inventor from a hybridization of two unnamed seedlings. The male parent of Eclipse was identified as 787071, an unnamed yellow decorative seedling originated from a cross between Vanguard, disclosed in U.S. Plant Pat. No. 4,555, and an unnamed seedling.

Eclipse was discovered and selected as one flowering plant within the progeny of the stated cross by William E. Duffett in February, 1980 in a controlled environment in Salinas, Calif.

The first act of asexual reproduction of Eclipse was accomplished when vegetative cuttings were taken from the initial selection in June, 1980 in a controlled environment in Salinas, Calif. by a technician working under formulations established and supervised by William E. Duffett. Horticultural examination of selected units initiated July 15, 1981 has demonstrated that the combination of characteristics as herein disclosed for Eclipse are firmly fixed and are retained through successive generations of asexual reproduction.

Eclipse has not been observed under all possible environmental conditions. The phenotype may vary significantly with variations in environment such as temperature, light intensity and day length. The observations, measurements and comparisons describe plants grown in Salinas, Calif. and Leamington, Canada under greenhouse conditions which approximate those generally used in commercial practice.

The following traits have been repeatedly observed and are determined to be basic characteristics of Eclipse which in combination distinguish this chrysanthemum as a new and distinct cultivar:

(1) Semi-incurved capitulum form;

(2) Decorative capitulum type;

(3) Deep lemon yellow ray floret color;

(4) Diameter across face of capitulum ranging from 100 to 120 mm. at maturity;

(5) Uniform nine week photoperiodic flowering response to short days;

(6) Medium plant height, requiring 1–2 long day weeks prior to pinch and short days, and one application of 2500 ppm B-9 14 days after the beginning of short days to attain a flowered plant height of 25 to 38 cm.; and (7) Prolific, spreading branching pattern.

The accompanying photographic drawings depict typical foliage and inflorescence characteristics of Eclipse, Sheet 1 is a color photograph of a plant of Eclipse grown as a pinched, disbudded pot mum, with colors being as accurate as possible with renditions of this type. Sheet 2 is a black and white photograph of three views of the inflorescence of Eclipse. Sheet 3 shows the leaves of Eclipse in three stages of development (mature, intermediate, immature).

Of the many commercial cultivars known to the present inventor, the most similar in comparison to Eclipse are the unpatented cultivar Bright Golden Anne, and Wild Honey, disclosed in U.S. Plant Pat. No. 3,359. Reference is made to attached Chart A which compares certain characteristics of Eclipse to those same characteristics of Bright Golden Anne and Wild Honey.

Both Wild Honey and Bright Golden Anne develop a deeper golden yellow color than Eclipse but they will tinge light bronze with a cool finish. Eclipse maintains color clarity the year round.

Eclipse expresses a more incurved form; all three cultivars classify as decorative capitulum types. The capitulum diameter of Wild Honey averages 25 mm. smaller than Eclipse or Bright Golden Anne, which are similar in size.

Wild Honey and Bright Golden Anne display an upright branching pattern. Eclipse spreads its breaks at a wider angle to the main stem.

Eclipse and Wild Honey have similar 9 week response time, with good tolerance of high summer temperatures. Bright Golden Anne requires 10 weeks for flower maturation and delays to 11 weeks under high summer temperatures.

In the following description, color references are made to The Royal Horticultural Society Colour Chart. The color values were determined between 8:30 A.M. and 9:00 A.M. on Dec. 6, 1982 under 150 foot-candle light intensity at Salinas, Calif.

CLASSIFICATION

Botanical: *Chrysanthemum morifolium,* Ramat., cv. Eclipse.

Commercial: Disbud decorative pot mum.

INFLORESCENCE

Capitulum:

*Form.*—Semi-incurved.

*Type.*—Decorative.

*Diameter across face.*—100 To 120 mm.

Corolla of ray florets:

*Color (general tonality from a distance of three meters).*—Deep lemon yellow.

*Color (abaxial).*—5A-B.

*Color (adaxial).*—5C.

*Shape.*—Oblong, pointed tip sometimes showing a small notch.

Corolla of disc florets:

*Color (mature).*—1B.

*Color (immature).*—154A.

Reproductive organs:

*Androecium.*—Present disc florets only; scant pollen.

*Gynoecium.*—Present both ray and disc florets.

PLANT

General appearance:

*Height.*—Medium; 25 to 38 cm. given 2 long day weeks after pinch and lights out, and one application of 2500 ppm B-9 SP after lights out.

*Branching pattern.*—Prolific and spreading.

Foliage:

*Color (abaxial).*—147B.

*Color (adaxial).*—147D.

*Shape.*—Broad, shallow lobes. Small serrations.

CHART A

COMPARISON OF ECLIPSE, BRIGHT GOLDEN ANNE AND WILD HONEY

| CULTIVAR | RAY FLORET COLOR | CAPITULUM FORM AND TYPE | BRANCHING PATTERN |
|---|---|---|---|
| ECLIPSE | DEEP LEMON YELLOW CLEAR COLOR YEAR ROUND | SEMI-INCURVED DECORATIVE | SPREADING |
| BRIGHT GOLDEN ANNE | GOLDEN YELLOW | FLAT DECORATIVE | UPRIGHT |
| WILD HONEY | GOLDEN YELLOW TINGES LIGHT BRONZE IN WINTER | FLAT DECORATIVE | UPRIGHT |

| CULTIVAR | DIAMETER ACROSS FACE OF CAPITULUM | PLANT HEIGHT | FLOWERING RESPONSE PERIOD |
|---|---|---|---|
| ECLIPSE | 100 to 120 mm. | MEDIUM 25 to 38 cm. | 9 WEEK GOOD TOLERANCE OF HIGH TEMPERATURE |
| BRIGHT GOLDEN ANNE | 100 to 120 mm. | TALL 30 to 45 cm. | 10 WEEK POOR TOLERANCE OF HIGH TEMPERATURE |
| WILD HONEY | 75 to 100 mm. | TALL 28 to 40 cm. | 9 WEEK GOOD TOLERANCE OF HIGH TEMPERATURE |

COMPARISONS MADE OF PLANTS GROWN AS PINCHED, DISBUDDED POT MUMS IN SALINAS, CALIFORNIA AND LEAMINGTON, CANADA

I claim:

1. A new and distinct cultivar of *Chrysanthemum morifolium,* Ramat., named Eclipse, as described and illustrated, and particularly characterized as to uniqueness by the combined characteristics of semi-incurved capitulum form; decorative capitulum type; deep lemon yellow ray floret color; diameter across face of capitulum ranging from 100 to 120 mm. at maturity; uniform nine week flowering response; medium plant height and spreading branching pattern.

* * * * *

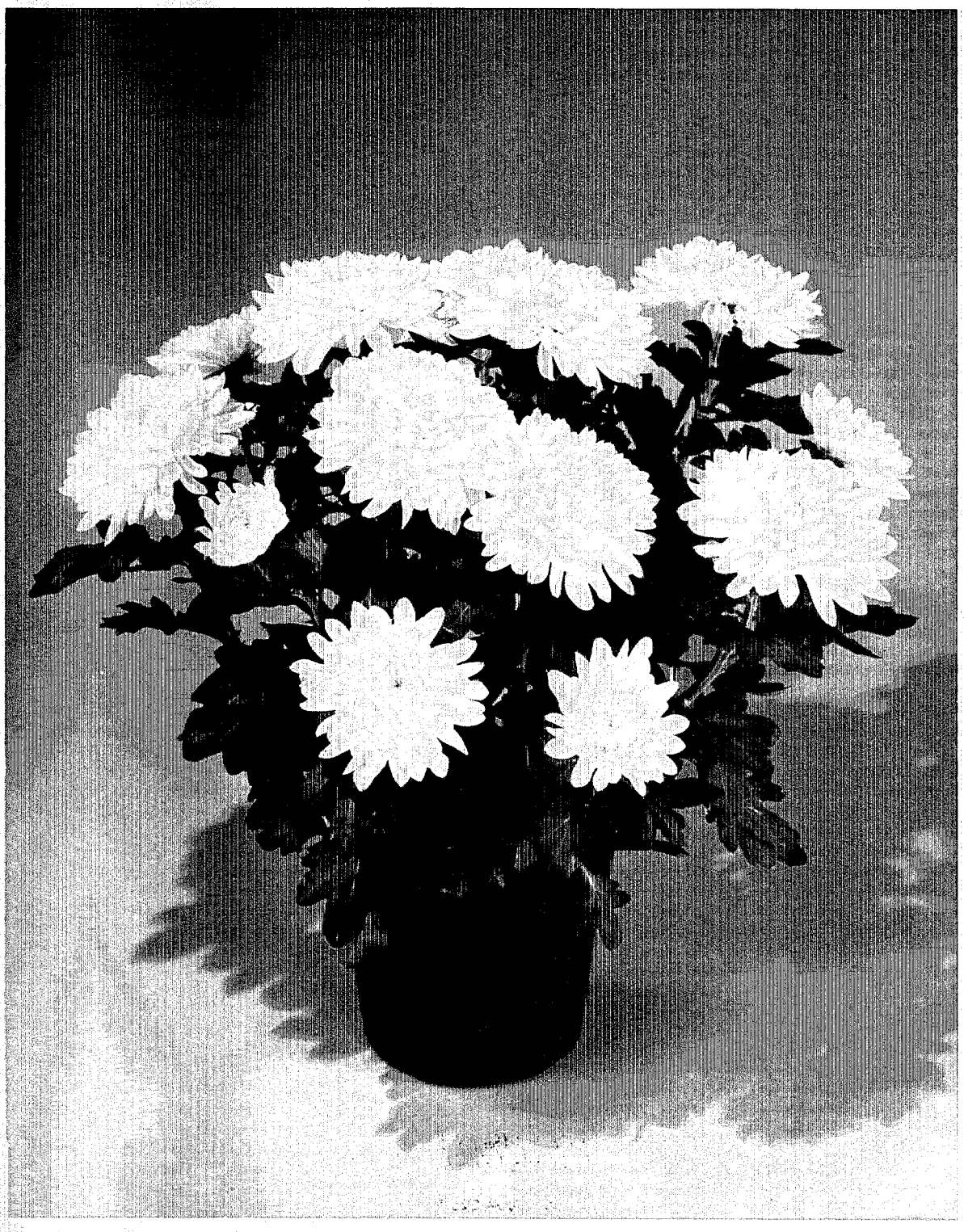

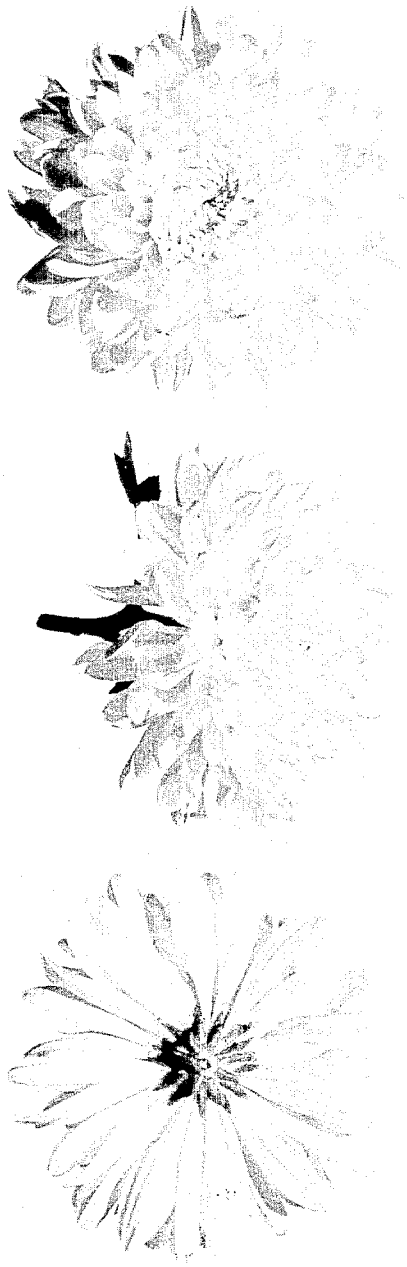

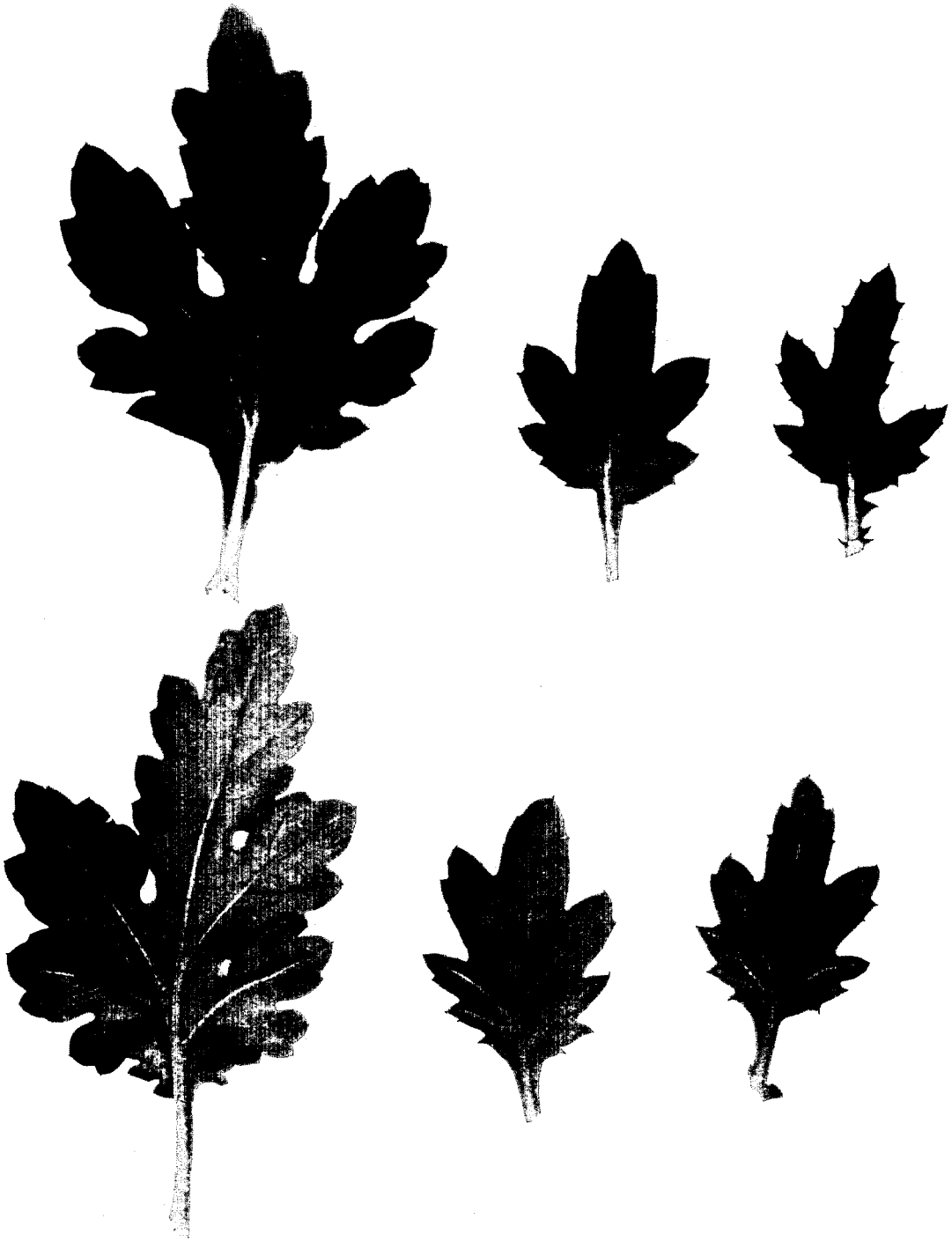

UNITED STATES PATENT AND TRADEMARK OFFICE

CERTIFICATE OF CORRECTION

PATENT NO. : Plant Patent No. 5402

DATED : February 5, 1985

INVENTOR(S) : William E. Duffett

It is certified that error appears in the above—identified patent and that said Letters Patent is hereby corrected as shown below:

In Column 2, line 18, "Eclipse, Sheet" should be --Eclipse. Sheet--.

In Column 3, line 6, "Dec. 6, 1982" should be --Dec. 16, 1982--.

In Column 3, line 41, "weeks after pinch" should be --weeks before pinch--.

Signed and Sealed this

*Eighth* Day of *October 1985*

[SEAL]

*Attest:*

*Attesting Officer*

DONALD J. QUIGG

*Commissioner of Patents and Trademarks—Designate*